(12) United States Patent
Iyengar et al.

(10) Patent No.: US 6,508,108 B1
(45) Date of Patent: Jan. 21, 2003

(54) SETTLING TEST FOR MAGNETORHEOLOGICAL FLUIDS

(75) Inventors: Vardarajan R. Iyengar, Pontiac, MI (US); Michael W. Hurtt, Waynesville, OH (US); Charles T. West, Dayton, OH (US); Justin A. Rindler, Kettering, OH (US); Perry K. Arnold, Beavercreek, OH (US)

(73) Assignee: Delphi Technologies, Inc., Troy, MI (US)

( * ) Notice: Subject to any disclaimer, the term of this patent is extended or adjusted under 35 U.S.C. 154(b) by 0 days.

(21) Appl. No.: 10/015,340

(22) Filed: Dec. 13, 2001

(51) Int. Cl.⁷ .................. G01N 15/04; G01N 11/00
(52) U.S. Cl. .................. 73/61.63; 73/61.74
(58) Field of Search .................. 73/61.62, 61.63, 73/61.65, 61.66, 61.71, 61.74, 61.76

(56) References Cited

U.S. PATENT DOCUMENTS

| | | | |
|---|---|---|---|
| 5,645,752 A | 7/1997 | Weiss et al. |
| 6,132,633 A | 10/2000 | Carlson |
| 6,203,717 B1 | 3/2001 | Munoz et al. |
| 6,260,675 B1 | 7/2001 | Muhlenkamp |
| 6,279,700 B1 | 8/2001 | Lisenker et al. |
| 6,279,701 B1 | 8/2001 | Namuduri et al. |
| 6,290,033 B1 | 9/2001 | Oliver |
| 6,296,088 B1 | 10/2001 | Carlson |
| 6,311,810 B1 | 11/2001 | Hopkins et al. |

*Primary Examiner*—Hezron Williams
*Assistant Examiner*—Jay L. Politzer
(74) *Attorney, Agent, or Firm*—Scott A. McBain

(57) ABSTRACT

A method of testing magnetorheological fluid comprises cycling the fluid at an elevated temperature, allowing the fluid to stand, performance testing the fluid, cycling the fluid at superimposed frequencies, and noting settling characteristics of the fluid.

20 Claims, 1 Drawing Sheet

SETTLING TEST FOR MAGNETORHEOLOGICAL FLUIDS

TECHNICAL FIELD OF THE INVENTION

The present invention relates to suspension systems for motor vehicles, and more particularly to a system for measuring the settling of magnetorheological fluids in a suspension damper.

BACKGROUND OF THE INVENTION

A suspension damper, commonly referred to as a shock absorber, reduces the amplitude of resilient suspension excursions between a sprung mass and an unsprung mass of a motor vehicle by converting into work a fraction of the kinetic energy of the sprung mass. Typically, a suspension damper includes a fluid-filled cylinder tube connected to the unsprung mass, a piston in the cylinder tube connected by a rod to the sprung mass, and valves on the piston which throttle fluid flow across the piston during compression and rebound strokes of the suspension damper attributable to relative suspension excursions between the sprung and unsprung masses.

Some dampers use magnetorheological (MR) fluids, which have been found to have desirable electro-magnetomechanical interactive properties. MR fluids that comprise suspensions of magnetic particles such as iron or iron alloys in a fluid medium have flow characteristics that can change by several orders of magnitude within milliseconds when subjected to a suitable magnetic field due to alignment of the magnetic particles to form a structure that resists deformation.

MR fluids used in dampers can settle, i.e. the iron may separate from the liquid and form a sediment at the bottom of the damper. If the settling is severe and the iron sediment is hard-packed, then the performance of the damper may be compromised. Many settling tests have been used in order to predict the behavior of an MR fluid in a damper. These include quiescent settling in a calibrated cylinder, and settling after the fluid was heated and sheared in a mixer. U.S. Pat. No. 5,645,752 discusses the use of ASTM tests D869 and D1309 originally intended to measure settling of paints. U.S. Pat. No. 6,203,717 discloses a settling test in which MR fluid is repeatedly thermally cycled, and the degree of settling is evaluated using a penetrometer test. Both of these patents and the ASTM tests they discuss are hereby incorporated by reference.

None of these tests adequately predict the settling behavior of MR fluid in a damper.

SUMMARY OF THE INVENTION

The present invention is a method of testing magnetorheological fluid. The method comprises cycling the fluid at an elevated temperature, allowing the fluid to stand, performance testing the fluid, cycling the fluid at superimposed frequencies, and noting settling characteristics of the fluid.

Accordingly, it is an object of the present invention to provide a method of the type described above which distinguishes between MR fluids that settle hard and those that do not.

Another object of the present invention is to provide a method of the type described above that accounts for the fact that the rate and tendency of MR fluid sedimentation may vary with the amount of durability testing to which a damper has been exposed.

Still another object of the present invention is to provide a method of the type described above that tests the damper and fluid system for sedimentation tendencies at relatively frequent and narrow time intervals with respect to the anticipated overall life of a damper.

These and other features and advantages of the invention will become further apparent from the following detailed description of the presently preferred embodiments, read in conjunction with the accompanying drawing. The detailed description and drawing are merely illustrative of the invention rather than limiting, the scope of the invention being defined by the appended claims and equivalents thereof.

DETAILED DESCRIPTION OF THE PRESENTLY PREFERRED EMBODIMENTS

Figure 1:
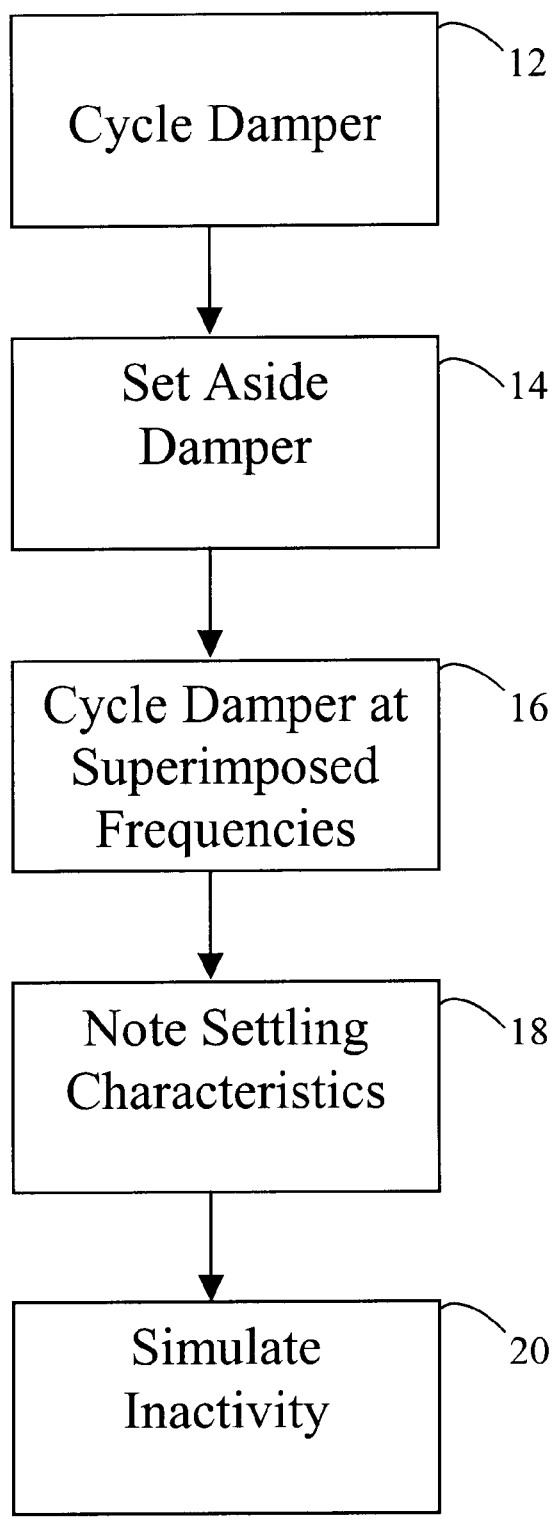
FIG. 1 is a block diagram of a method according to the present invention for testing for settling of MR fluid in a suspension damper.

FIG. 1 shows a block diagram of a method according to the present invention to predict the settling of MR fluids in dampers. The method preferably includes three separate tests, each of which must be satisfied by a candidate MR fluid. In the first test, the MR fluid is cycled in an actual or simulated damper for about sixty minutes while the external damper temperature is maintained in the range of about 110 degrees C, as shown by block 12. The damper is then set aside for a period of time, preferably in the range of about three days, after which a standard performance test is conducted as shown by block 14. In one embodiment of the performance test, the load required to displace the damper at an amplitude of plus or minus 50 mm and a frequency of 1.6 Hz is measured. A load/position data curve of the performance test is then examined for the presence of unexpected peaks or "load lumps" in the required load as compared to a similar curve for an acceptable sample. Load lumps in the load vs. displacement performance curve characterize settling in the MR fluid. This first test measures the effects of temperature and shear, and is useful, alone or in combination with a second test described below, in predicting the short to medium term settling performance of MR fluids in dampers.

A second test includes obtaining a sample of the candidate MR fluid, preferably but not necessarily new, and conducting a life test. The life test cycles the damper at two superimposed frequencies, as shown by block 16. In a preferred embodiment, the frequencies for this life test are 0.833 Hz and 10 Hz, with amplitudes of 50 mm and 12.5 mm, respectively. The damper temperature is maintained at 70 degrees C., and a side load of 100 is applied at a rod guide of the damper. Samples of the MR fluid, which may be in the range of about 10 ml, are taken at 10, 20, 30, 40, 50, 60, 70, and 100 thousand cycles of the lower frequency. These samples are poured into glass vials, preferably 4 dram vials 70 millimeters tall with a 21 millimeter outside diameter, until the vials are about half full. The settling characteristics of these samples are then noted, as indicated by block 18. An MR fluid is considered acceptable if a clear layer formed due to iron settling over a 24 hour period does not exceed 20% by volume. This second test measures the effects of temperature and high shear on the settling, and is useful, alone or in combination with the first test, in predicting the short to medium term settling performance of MR fluids in dampers.

A third test studies the effect of time on a sheared sample of the candidate MR fluid. From the second test above, the number of cycles at which the settling behavior is the worst is determined by measuring the heights of the clear layers of samples corresponding to different numbers of damper test cycles. A new MR fluid and damper is then cycled to precisely that number of cycles, after which the damper is tested according to ASTM D1309 to simulate six months of inactivity, as shown by block 20. The damper is then performance tested a second time, and the data are scrutinized for the presence of load lumps. The absence of load lumps indicates that the fluid is highly resistant to hard settling. This third test predicts the longer-range settling behavior of MR fluids in vehicle dampers.

The present invention thus provides a method which distinguishes between MR fluids that settle hard and those that do not exhibit significant settling in the damper. The present invention also accounts for the fact that the rate and tendency of MR fluid sedimentation may vary with the amount of durability testing to which a damper has been exposed. Thus, the iron powder in a particular fluid formulation/design may precipitate out of solution to form a clear layer of base fluid above a layer of fluid concentrated with iron powder after a predetermined period of static storage more readily than other formulations after being exposed to the exact same amount of shear history and temperature in a damper assembly. The present invention also tests the damper and fluid system for sedimentation tendencies at relatively frequent and narrow time intervals with respect to the anticipated overall life of a damper, in order to accurately capture the variation of this characteristic with time for any particular fluid and damper system.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

What is claimed is:

1. A method of testing magnetorheological fluid, the method comprising:

cycling the fluid at an elevated temperature;

allowing the fluid to stand;

performance testing the fluid;

cycling the fluid at superimposed frequencies; and noting settling characteristics of the fluid.

2. The method of claim 1 further comprising determining the number of cycles during the second cycling step at which settling of the fluid is greatest.

3. The method of claim 2 further comprising cycling the fluid a number of cycles generally equal to the determined number of cycles.

4. The method of claim 3 wherein the third cycling step is performed with a new sample of the fluid.

5. The method of claim 3 further comprising subjecting the fluid to a prolonged period of simulated or actual inactivity.

6. The method of claim 3 further comprising subjecting the fluid to a simulated period of inactivity not less than six months.

7. The method of claim 5 further comprising performance testing the fluid a second time.

8. The method of claim 1 wherein the elevated temperature is in the range of about 110 degrees C., and the fluid is cycled at the elevated temperature for about sixty minutes.

9. The method of claim 1 wherein the fluid is allowed to stand for about three days.

10. The method of claim 1 wherein the second cycling step is performed with a new sample of the fluid.

11. The method of claim 1 wherein one of the superimposed frequencies is below 1 Hz, and another of the superimposed frequencies is about 10 Hz.

12. The method of claim 1 wherein the second cycling step is performed at a second elevated temperature.

13. The method of claim 1 wherein the noting step is performed on a sample taken prior to 100,000 cycles of a lower of the superimposed frequencies.

14. A method of testing magnetorheological fluid, the method comprising:

cycling the fluid to determine the number of cycles at which settling of the fluid is greatest;

cycling a new sample of the fluid a number of cycles generally equal to the determined number of cycles;

subjecting the fluid to a prolonged period of simulated or actual inactivity; and performance testing the fluid.

15. A method of predicting settling of magnetorheological fluid in a class of dampers, the method comprising:

providing the fluid in a damper of the type for which the prediction is intended;

cycling the damper at an elevated external temperature;

allowing the damper to stand;

measuring a load required to displace the damper;

cycling the damper at superimposed frequencies; and noting settling characteristics of the fluid.

16. The method of claim 15 further comprising determining the number of cycles during the second cycling step at which settling of the fluid is greatest.

17. The method of claim 16 further comprising cycling the damper a number of cycles generally equal to the determined number of cycles.

18. The method of claim 17 wherein the second and third cycling steps are performed with new samples of the fluid.

19. The method of claim 17 further comprising subjecting the fluid to a prolonged period of simulated or actual inactivity.

20. The method of claim 19 further comprising measuring a second time a load required to displace the damper.

* * * * *